(12) United States Patent
Boustani et al.

(10) Patent No.: US 7,288,064 B2
(45) Date of Patent: Oct. 30, 2007

(54) GASTRIC RING

(75) Inventors: Roland Boustani, Orleans (FR); William Houard, Labastide Rouairoux (FR); Philippe Berret, St Paul et Valmalle (FR)

(73) Assignee: Textile Hi Tec, Labastide Rouairoux (FR)

( * ) Notice: Subject to any disclaimer, the term of this patent is extended or adjusted under 35 U.S.C. 154(b) by 0 days.

(21) Appl. No.: 10/516,350

(22) PCT Filed: May 30, 2003

(86) PCT No.: PCT/FR03/01631

§ 371 (c)(1),
(2), (4) Date: Mar. 31, 2006

(87) PCT Pub. No.: WO03/101352

PCT Pub. Date: Dec. 11, 2003

(65) Prior Publication Data

US 2006/0229696 A1 Oct. 12, 2006

(30) Foreign Application Priority Data

May 31, 2002 (FR) .................................. 02 06705

(51) Int. Cl.
*A61F 2/00* (2006.01)

(52) U.S. Cl. ........................... 600/37; 600/31; 606/151
(58) Field of Classification Search ............ 600/29–32, 600/37; 128/DIG. 25, 897–899; 606/151, 606/157, 201–203
See application file for complete search history.

(56) References Cited

U.S. PATENT DOCUMENTS

| 3,368,344 | A | | 2/1968 | Graetz |
| 4,955,913 | A | | 9/1990 | Robinson |
| 5,152,770 | A | | 10/1992 | Bengmark et al. |
| 5,449,368 | A | | 9/1995 | Kuzmak |
| 5,567,431 | A | * | 10/1996 | Vert et al. .................... 424/426 |

* cited by examiner

*Primary Examiner*—John P. Lacyk
(74) *Attorney, Agent, or Firm*—Millen, White, Zelano & Branigan, P.C.

(57) ABSTRACT

The gastric ring comprises an elongate element that can be deformed into a loop between a distal end portion and a proximal end portion, together with closure means suitable for folding the elongate element into a loop and for fastening the distal and proximal end portions together once they have been moved close to each other while looping the ring. At least the elongate element is made of a material that is resorbable, preferably over a period of about or less than 2 years, e.g. of a poly-α-hydroxy acid. The elongate element is constituted by a proximal link, a distal link, and intermediate links hinged about pivot axes.

21 Claims, 5 Drawing Sheets

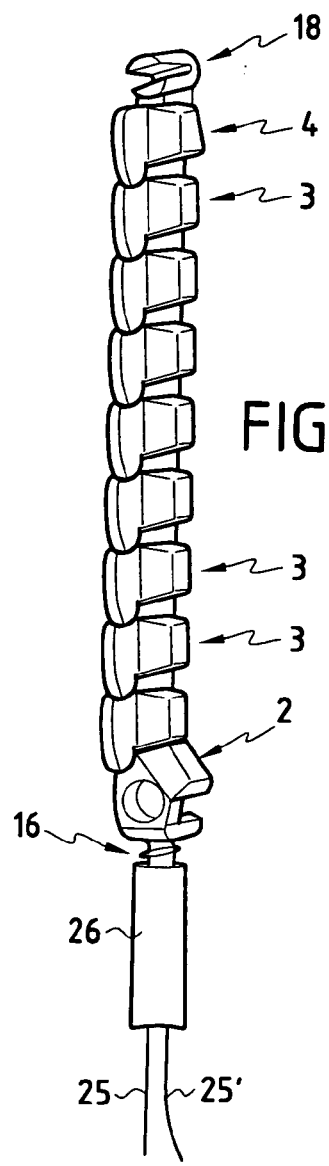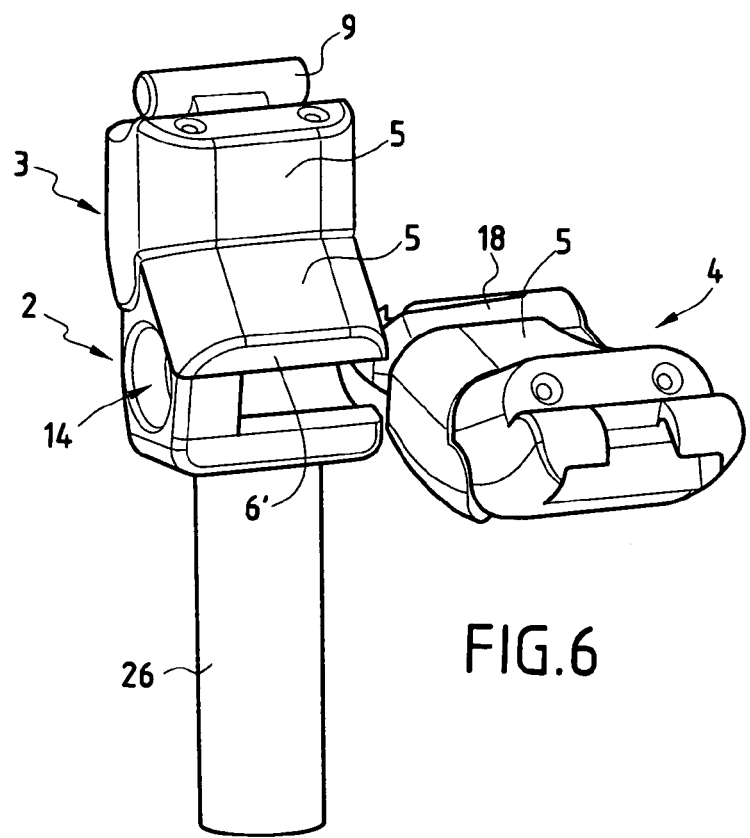

GASTRIC RING

The present invention relates to a gastric ring, also known as a gastroplasty ring or gastric band or a gastric constriction member.

BACKGROUND OF THE INVENTION

Fitting a gastric ring constitutes one of the techniques that have been developed for combating massive obesity from which an increasing number of people are suffering in developed countries.

Compared with other techniques, such as gastric bypass (BPG), or vertical banding gastroplasty (VGB), fitting a gastric ring presents the advantage of not changing the anatomy of the patient. Its principle is to reduce the diameter of the stomach opening, creating an anterior pocket of volume that is small so that the patient has a sensation of being sated after ingesting a minimal quantity of food.

Since its appearance in 1986, several models of gastric ring have been proposed that are suitable for being implanted by laparoscopic surgery. Nevertheless they all have structure that is substantially similar. They comprise a certain length of relatively narrow band made of a material that is sufficiently flexible to be capable of being looped, said band being provided with closure means acting between its distal and proximal ends. In addition, adjustment means suitable for being externally actuated enable the inside diameter of the gastric ring to be adjusted, once it has been put into place.

In the ring known as a Lap Band® or as LAGB®, the adjustable nature is obtained by an inside section of the ring being inflatable, said section being the part that is to come into contact with the stomach. A connection tube connects said inflatable section to a so-called "injection port". When the ring is put into place, the connection tube and the connection part are permanently implanted inside the patient's body, with the injection port being easily accessible. While the ring is being put into place, it is at minimum inflation. Its diameter is adjusted by injecting the inflation fluid into the injection port.

The gastric ring known as the Swedish Adjustable Gastric Band SAGB® differs from the Lap Band® mainly by its closure system which consists in a system having a tongue with a safety catch, the ring being closed by pulling on said tongue until the safety catch is reached. The ring known under the name Heliogast® differs from the first two likewise by its closure system which makes use of hydraulic locking.

In spite of its recognized effectiveness, in terms of loss of weight, the gastric ring technique is not without drawbacks, in particular due to the complications that can arise.

Some of these complications are associated with the presence of the injection port which might be faulty, and with the connection tube which might rupture. According to a recent study, more than 8% of the observed complications are due to those two causes. Changing the injection port requires further surgery under general anesthetic. A rupture in the connection tube requires further laparoscopic surgery.

The injection port may also be the seat of acute or chronic suppuration.

Finally, in terms of appearance, implanting the injection port leaves a scar that is 5 centimeters (cm) to 6 cm long.

Other known complications of the gastric ring technique consist in a phenomenon whereby the ring migrates in the gastro-gastric wall, and also in a phenomenon whereby the wall of the stomach slides through the ring. Even though some complications of this kind can occur soon after the ring has been implanted, most of them appear in the medium term, after several years.

OBJECTS AND SUMMARY OF THE INVENTION

The object of the Applicant is to propose a gastric ring which mitigates the above-mentioned drawbacks in full or in part.

In conventional manner, the invention provides a gastric ring of the type comprising an elongate element that is deformable into a loop between a distal end portion and a proximal end portion, and closure means suitable for folding said elongate element into a loop and for securing the distal and proximal end portions to each other once they have been brought close together by looping the ring.

In a manner characteristic of the invention, at least the elongate element is made of a resorbable material.

The resorbable nature of the elongate element which constitutes the body of the gastric ring makes it possible to limit the presence of said ring over time and thus limits those complications which are associated with such presence in the medium and long term. In addition, the non-definitive nature of fitting a ring of the invention has an important psychological impact on the choice made by the patient. After a probationary period that is limited in time, the patient can stop the experiment, or else, if so desired, proceed with a new implant that is either definitive or else once again limited in time.

The elongate element is preferably made of a material that is resorbable slowly of a period of the order of or less than 2 years, and more preferably over a period lying in the range 16 months to 24 months.

Firstly, this period of time corresponds to the period during which effective loss of weight takes place, prior to weight stabilizing.

Secondly, it is after this period that the presence of the gastric ring leads to increased risk in terms of migration, perforation, or infection, in terms of progressive dilation of the esophagus, and in terms of behavior disorders. These risks are thus eliminated by choosing this resorption time.

The ring is essentially made of biodegradable materials of natural or synthetic origin such as:

polylactide, polyglyoclide, poly ε-caprolactone;

polyhydroxybutyrate, polyhydroxyvalerate;

polycarbonates;

cellulose, polysaccharides, starch, . . . ;

. . . homopolymers, copolymers, and derivatives thereof.

The material constituting the elongate element is preferably a poly-α-hydroxy acid, which is a family of bioresorbable polymers.

Advantageously, amongst known poly-α-hydroxy acids, use is made of a lactic polyacid, and more particularly a poly (L-lactide-co-D,L-lactide). At the final stage of degradation, lactic acid or glycolic acid are obtained, being respectively a metabolite and a pre-metabolite that are natural in the human body. These acids are oxidized in the organism into pyruvic acid which is itself metabolized into carbon dioxide gas and water via the tri-carboxylic acid cycle. The elongate element of the gastric ring made of such a material is thus completely resorbed in the body of the patient. This resorption takes place at a speed that varies as a function of various factors such as chemical composition and crystal content, molecular mass, and degree of polymerization. For example, the greater the crystal content of the lactic polyacid, the slower it is resorbed.

In an embodiment of the gastric ring of the invention, the elongate element is constituted by a set of juxtaposed links. It is thus made up of a proximal link, a distal link, and intermediate links.

By way of example, each link is generally polyhedral in shape with an inner face for coming into contact with the stomach when the ring is put into place, and two internal end faces, with at least those portions thereof that are situated close to the inner face being oblique and converging radially so that when the ring is closed all of said radial portions of the internal end faces are pressed one against another, and the inner faces of the links constitute a substantially continuous constriction surface.

In order to be suitable for being introduced by means of a trocar, it is necessary for all of the intermediate links to be connected to one another. Each intermediate link preferably includes a shoulder projecting from a first internal end face to form a pivot axis between said link and a first adjacent link, and a recess in a second internal end face forming a housing for the shoulder of a second adjacent link, the shoulder and the recess being of dimensions that are suitable for being mutually interengaged.

The closure means must enable the elongate element to be looped to itself and the distal and proximal end portions to be connected together, and in particular they must enable the distal link to be connected to the proximal link.

In an embodiment, the closure means comprise at least one tie which is secured to at least one of the proximal and distal end portions.

Advantageously, said tie(s) is/are resorbable over a resorption period that is longer than the resorption period for the elongate element.

In this particular disposition, the gastric ring retains its effectiveness even when the elongate element and in particular the links have lost a large fraction of their mechanical strength.

Optionally, said tie(s) is/are not resorbable, providing the presence thereof in the body of the patient after the elongate element has been fully resorbed does not present any drawback, as is the case when the tie is to be found in a free state that is not tight about the stomach. This therefore applies when the tie does not interconnect the distal and proximal end portions.

In a preferred embodiment, using juxtaposed links to make up the elongate element, each link has two through holes forming two alignments of holes through the set of links so as to allow a single tie to pass along the elongate element twice, from the proximal link to the distal link via the first alignment of holes and then from the distal link to the proximal link via the second alignment of holes. In order to cause the elongate element to become curved, it suffices to take hold of the two free ends of the tie and apply traction thereto, while keeping the proximal link in place so as to cause the distal link to move towards the proximal link, and then to knot the two free ends of the link together in order to hold the elongate element in its looped configuration.

Preferably, in order to maintain the elongate element in its looped configuration, the closure means include locking means formed, at least in part, in the proximal and distal end portions of the elongate element, and in particular in the proximal and distal links.

For example, one end portion has a male engagement element while the other end portion has a female engagement element. In particular, the male element may be a stud and the female element may be a recess. When applied to links, the recess may be formed, for example, in an outer end face of the proximal or the distal link. While the ring is being put into place, the links are curved in the form of a turn with the distal link moving to beside the proximal link, after which it suffices for the operator to move said two links towards each other so as to engage the stud of one of them into the recess of the other, thereby locking the ring.

In the embodiment where the closure means include a tie, advantageously the proximal end portion, possibly the proximal link, includes a tube fitting for passing the two free ends of the tie; this tube fitting is preferably shaped to enable it to be secured to a ring introduction ancillary. In particular, it may be threaded to enable it to be screw-fastened to said ancillary. Under such circumstances, it is also preferable to provide a cap for closing the tube fitting, the cap being pierced by a through hole for passing the two free ends of the tie, said cap covering the threaded portion of the tube fitting after the ring has been put into place and the ancillary has been withdrawn.

BRIEF DESCRIPTION OF THE DRAWINGS

The present invention will be understood on reading the following description of an embodiment of a resorbable gastric ring, made up of a juxtaposition of lactic polyacid links provided with a non-resorbable closure tie, and shown in the accompanying drawings, in which:

FIGS. 5, 6, and 7 show steps in putting the gastric ring into place, with the ancillary being shown in part.

MORE DETAILED DESCRIPTION

Figure 1:
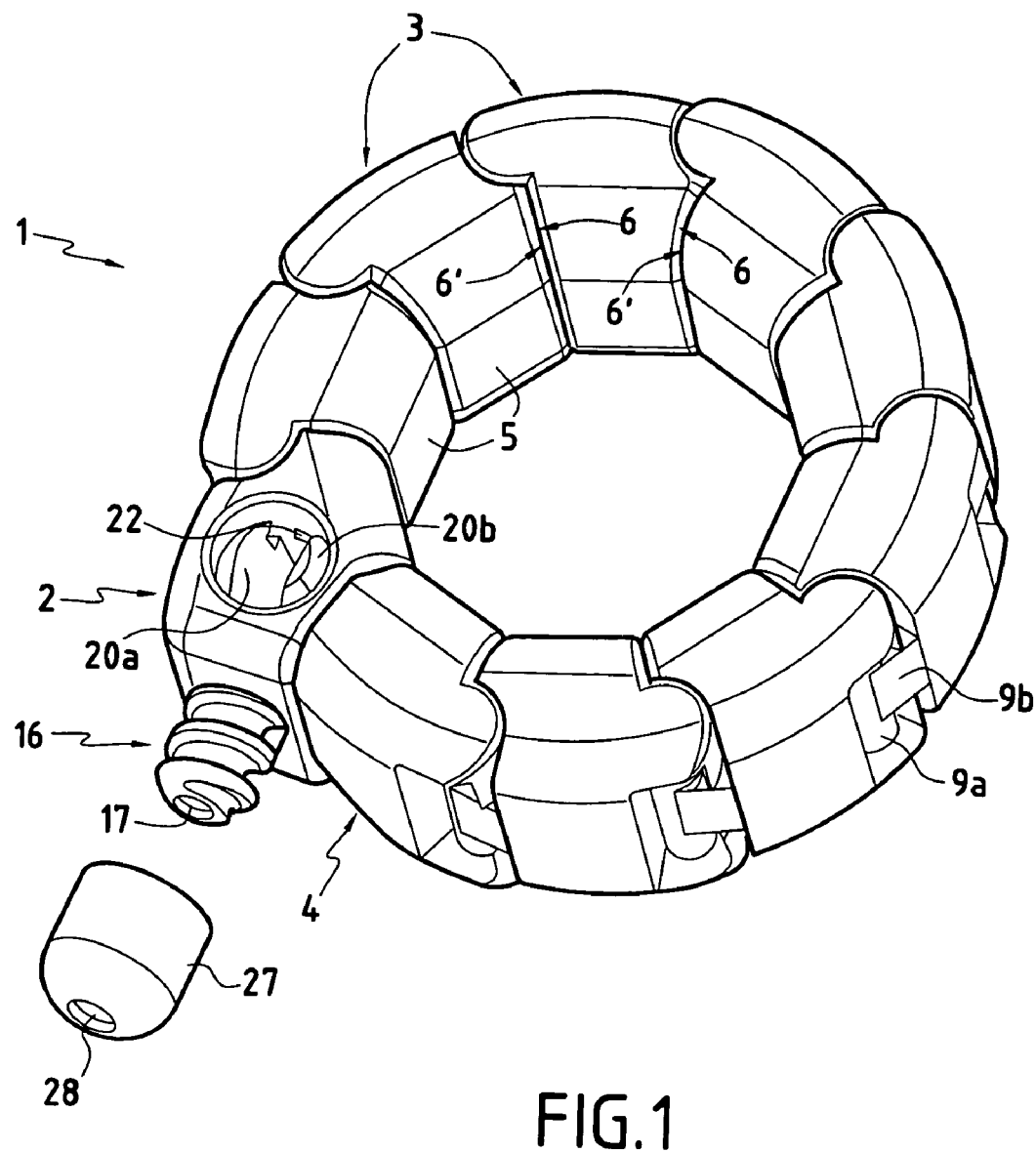
FIG. 1 is a diagrammatic perspective view of the ring in its looped and locked position.

The gastric ring of the present invention is characterized by its temporary nature, due to the fact that the elongate element constituting the main body of said ring is bioresorbable. Thus, unlike known gastric rings, the ring of the present invention is intended to constrict the stomach for a predetermined period only, without requiring new surgery at the end of said period. The resorbable material is selected so as to enable the duration of said period to be adjusted. A preferred period is considered as lying in the range 16 months to 24 months, and in any event of the order of or less than 2 years. Nevertheless, this is not exclusive, and in particular circumstances it might be possible to propose gastric rings for temporary use of shorter or longer duration.

In the embodiment described below, the gastric ring is not adjustable in size. Nevertheless, the present invention is not limited to this feature. An adjustable gastric ring of structure analogous to that of the known rings outlined above, could present a predetermined operating lifetime by virtue of its elongate element being made to be bioresorbable, by appropriately selecting the material from which said elongate element is made, said material presenting the desired bioresorbable nature. Nevertheless, under such circumstances, there remain the drawbacks associated with the presence of special means for enabling the diameter of the ring to be adjusted, unless said means are likewise made of a bioresorbable material.

Resorption of the ring, associated with its optionally non-adjustable nature, also gives rise to a reduction in cost, by virtue of reducing or eliminating certain post-operative checks, and thus by lowering the risk of complications associated with such checks, whether they involve taking X-rays of the stomach, or making repeated punctures.

The gastric ring 1 described in greater detail below has its elongate element made up of juxtaposed links, each link being a one-piece part made of a bioresorbable rigid material that is also biocompatible.

In a specific embodiment, the selected bioresorbable material is a poly-α-hydroxy acid, and more precisely a lactic polyacid. This polymer loses its mechanical properties progressively until it is completely absorbed. It presents a skeleton that is sensitive to hydrolysis. It is degraded by the combined effect of two phenomena, namely water penetrating into its matrix leading to short polymer chains being formed by breaking ester bonds, and migration or diffusion of these short chains to the outside. With rigid one-piece parts such as the links of the present gastric ring, the diffusion coefficient of water through the polymer matrix is greater than the migration coefficient of the products of hydrolysis. As a result, degradation is observed to take place more quickly in the core of the link that at its periphery, so the gastric ring remains effective during a longer period because it is its inner periphery that applies constriction to the stomach.

At the final stage of resorption of the lactic polyacid, lactic acid or glycolic acid is/are obtained which are respectively a natural metabolite and a natural pre-metabolite of the human body. These lactic and glycolic acids are oxidized by the organism into pyruvic acid which is itself metabolized into carbon dioxide gas and water, via the tri-carboxylic acid cycle.

Thus, the gastric ring of the present invention is completely resorbed in the body of the patient, with this resorption taking place at a speed that is variable as a function of the characteristics of the resorbable material used.

With poly-α-hydroxy acid, the factors that influence resorption time are, in particular, chemical composition and crystal content, molecular mass and degree of polymerization, the morphology of the part and in particular whether the part is a one-piece part or a film, the residual monomer content and the presence of possible other impurities, the dimensions of the part, the way in which it is sterilized, the site where the polymer is implanted in the body, . . . . Amongst the factors that are the most important, it is important to observe the crystal content. The greater the crystal content of a poly-α-hydroxy acid, the slower it will be resorbed.

For a lactic polyacid, it is possible to have an influence on crystal content by using a copolymer based on the L-lactide monomer and the D,L-lactide monomer. Preferably, a copolymer is used having a molar ratio of L-lactide to D,L-lactide that is of the order of 70/30 to 80/20. Such a lactic polyacid loses its mechanical properties after a few months, but it is resorbed into the body only after a duration that is considerably longer, and is a function in particular of the site in which it is implanted, and that duration may be of the order of 2 years, which is an appropriate duration as explained above.

In the example shown, the gastric ring 1 is made up of ten juxtaposed links, i.e. a proximal link 2, eight intermediate links 3, and a distal link 4.

In FIG. 1, the gastric ring 1 is shown in its configuration for constriction around the stomach, with the set of juxtaposed links being folded to form a loop, the proximal and distal links 2 and 4 being locked together, with said folding into the form of a loop and said locking being obtained by closure means described in greater detail below.

In the example shown, it should be observed that the inner surface of the gastric ring 1 that comes into contact with the stomach is of a polygonal configuration having ten faces, i.e. it is not circular. This disposition does not spoil the effectiveness of the ring in terms of constriction. It would be equally possible to attenuate this polygonal configuration by giving the inner faces 5 of each of the links 2, 3, 4 a somewhat concave shape.

Figure 2:
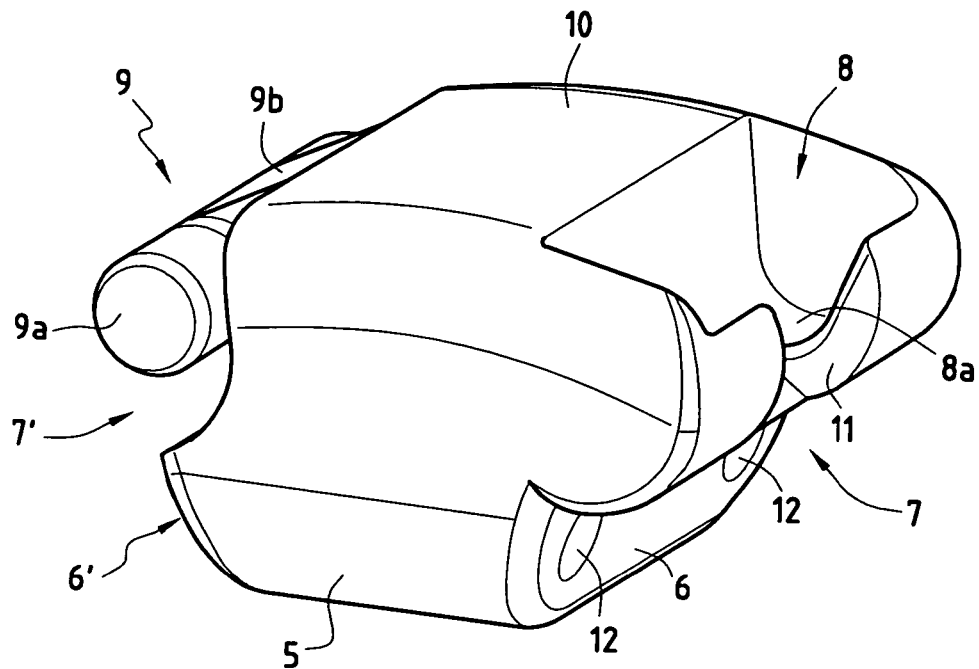
FIG. 2 is a diagrammatic perspective view of an intermediate link.

FIG. 2 shows an intermediate link 3 seen in perspective. The intermediate link 3 is generally in the form of a polyhedron having three determining faces, namely: its inner face 5 and two internal end faces 7 and 7', and more precisely the portions 6 and 6' of these internal end faces 7 and 7' that are situated close to the inner face 5. The inner face 5 (visible in FIG. 1) is for coming into contact with the stomach when the ring 1 is put into place. The portions 6, 6' of the two internal end faces 7, 7' are oblique and converge radially so that when the ring 1 is closed, all of said radial portions 6, 6', including those of the proximal and distal links 2 and 4, of said internal end faces are pressed one against another. The inner faces 5 of all of the links thus constitute a substantially continuous surface for constricting the stomach.

It will be understood that for a gastric ring 1 made up of ten links, as in the example shown, the angle α formed between the two portions 6, 6' of the two internal end faces 7, 7' needs to be 36°.

Given that the set of links making up the elongate element of the gastric ring 1 must be suitable for being introduced while in the rectilinear state by using a trocar, it is necessary for the links to be connected to one another. For this purpose, each intermediate link 3 includes hinge and pivot elements constituted by a recess 8 and by a shoulder 9. The recess 8 is formed in the upper portion of the link, after the portion 6 and opens out into the outer face 10 and into the internal end face 7. The shoulder 9 projects from the other internal end face 7' in the upper zone of the link, after the portion 6'. The shapes of the recess 8 and of the shoulder 9 are such that the shoulder 9 of a given intermediate link 3 is suitable for penetrating into the recess 8 of the link that is immediately adjacent to the given link, while the recess 8 of the given link is suitable for receiving the shoulder 9 of the link that is immediately adjacent thereto.

In the example shown in FIG. 2, the shoulder 9 is constituted by a cylindrical portion 9a constituting the pivot axis for folding the various links during closure of the ring, and a connection portion 9b between said cylindrical portion 9a and the internal end face 7' of the link 3.

The recess 8 forms a cavity having a semicircular bottom 8a for receiving by mutual engagement the cylindrical portion 9a of a shoulder 9. This cavity 8 is open both to the internal end face 7 and also to the outer face 10 of the link 3, i.e. the face which is opposite from the inner face 5. This second opening 11 allows the connection portion 9b of the shoulder 9 of the adjacent link to pass through when the various links are hinged to one another. Each link, and in particular each intermediate link 3, has two through holes 12 passing right through the link between the two radial portions 6, 6' of the internal end faces 7, 7'.

Figure 3:
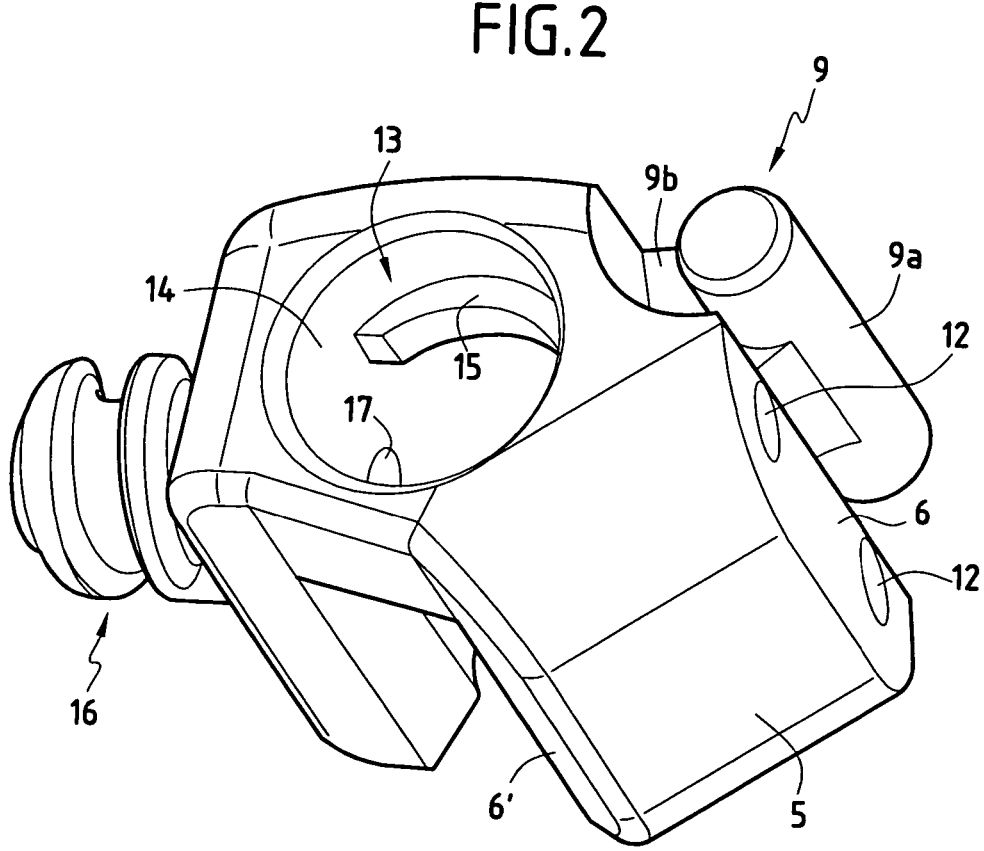
FIG. 3 is a diagrammatic perspective view of the proximal link.
Figure 4:
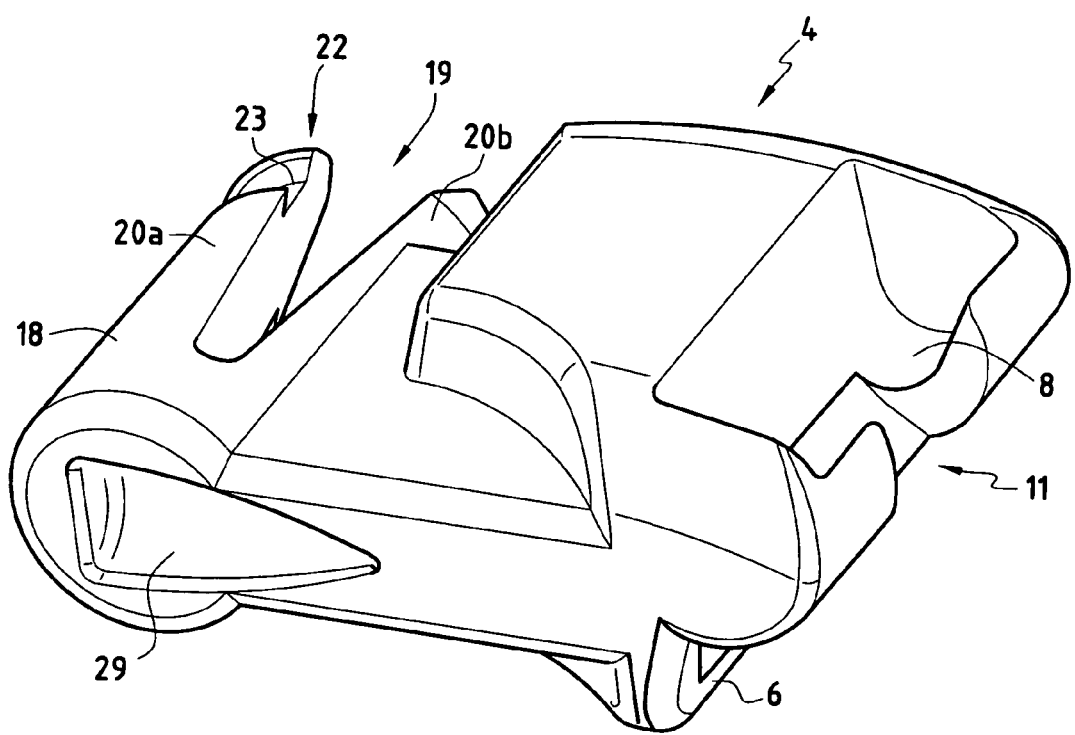
FIG. 4 is a diagrammatic perspective view of the distal link.
Figure 7:
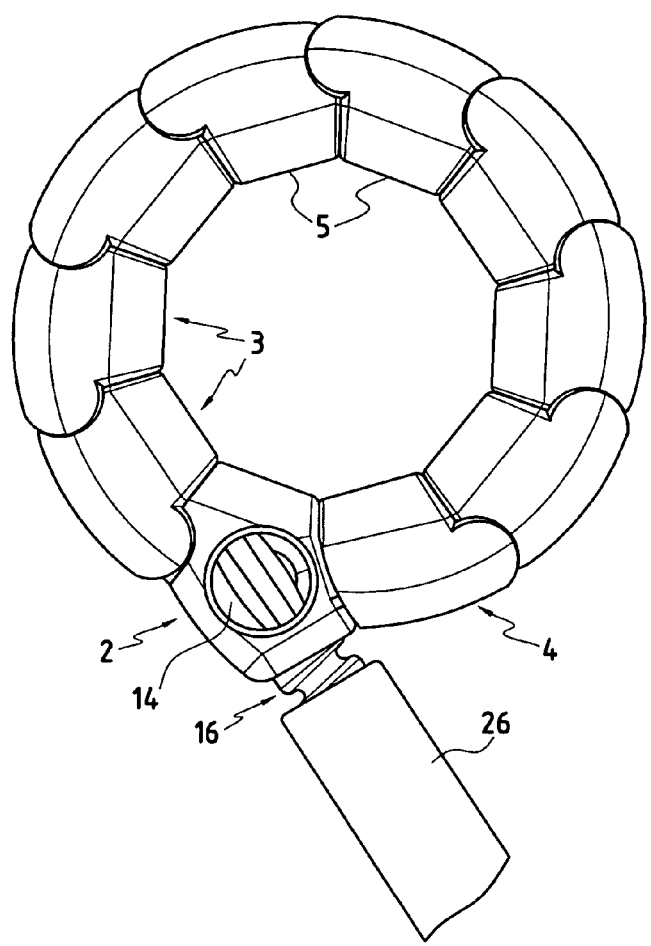
Figure 8:
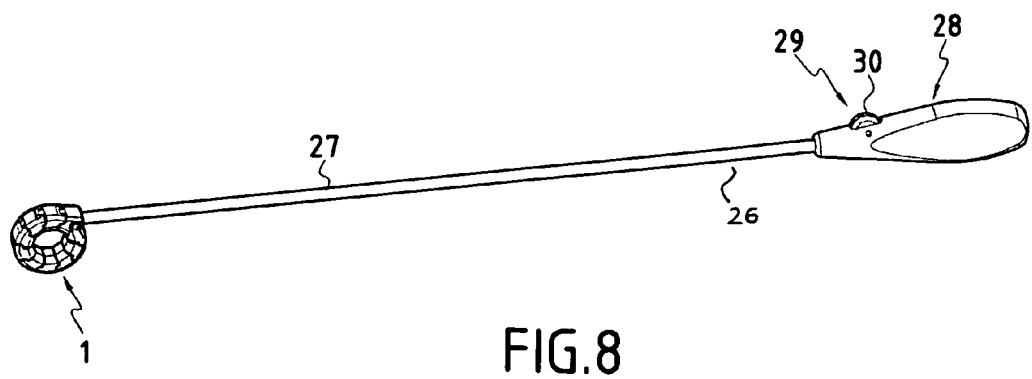
FIG. 8 is a diagrammatic perspective view of the gastric ring in the looped state and carried by the ancillary.

FIGS. 3 and 4 show respectively the proximal link 2 and the distal link 4. In these figures, the same references are used again for those portions that these links have in common with an intermediate link 3.

Like all of the intermediate links 3, the proximal link 2 has an inter face 5, two through holes 12, and a shoulder 9 formed by a cylindrical portion 9a and a connection portion 9b. However it does have a recess 8, with locking to the distal link 4 not taking place via a pivot hinge, but via specific locking means formed in the proximal link 2 and the distal link 4 and suitable for co-operating with each other.

The locking means of the proximal link 2 consist in a female engagement element 13 formed by a transverse recess 14 that is cylindrical, having an inside wall provided with an abutment 15 that is partially annular and that projects towards the inside of the recess 14.

The proximal link 2 also has a tube fitting 16 pierced by a through hole 17 and having its outer peripheral surface threaded, in order to enable the proximal link 2 to be screw-fastened to an ancillary 26 for use while putting the gastric ring 1 in place.

It should be observed that unlike an intermediate link 3 or the distal link 4, the two through holes 12 do not open out into the second internal end face 6', but into the transverse recess 14 in the through hole 17.

Like all the intermediate links 3, the distal link 4 has a recess 8 with an opening 11, and two through holes 12 that are not visible in FIG. 4.

The locking means of the distal link 4 for locking with the proximal link 2 consist in a transverse stud 18 of generally cylindrical configuration, having a notch 19 subdividing said stud 18 into two branches, a first branch 20a at the end and a second branch 20b that is connected to the remainder of the distal link 4 via an intermediate portion 21. As can be seen clearly on examining FIG. 4, since the notch 19 extends over only a fraction of the width of the link 4, the first branch 20a at the end presents a degree of flexibility relative to the second branch 20b. The ends 22 of the two branches 20a and 20b are chamfered so as to facilitate penetration of the stud 18 into the recess 14 in the proximal link 2. In addition, towards said chamfered end 22, the flexible branch 20a presents a partially annular groove 23 suitable for receiving the abutment 15 of the proximal link 2.

In addition to the above-described locking means, the means for closing the gastric ring 1 comprise means enabling the set of juxtaposed links to be folded into the form of a loop so that the distal link 4 can come up to and immediately beside the proximal link 2 so as to enable them to be locked together. The folding means comprise a tie passing through the through holes 12 in all of the links, and also through the through hole 17 in the tube fitting 16 of the proximal link 2. More precisely, when the links are in rectilinear alignment as shown in FIG. 5, the through holes 12 constitute two parallel alignments for the tie 24. The tie 24 passes firstly along one of the two alignments from the proximal link 2 to the distal link 4, and then back along the other alignment from the distal link back to the proximal link 2. The two free ends 25 and 25' of said tie 24 are passed together through the hole 17 in the tube fitting 16 and also along the ancillary 26 which is screwed onto the tube fitting 16 and which is intended to enable the gastric ring 1 to be held in its rectilinear configuration as shown in FIG. 5. Naturally, while the gastric ring is being introduced in this configuration, it is disposed inside a trocar that is not shown in FIG. 5.

Given that the tie 24 is offset relative to the cylindrical portions 9a of the shoulders 9 that act as pivot axes, when the practitioner exerts traction on the two free end 25, 25', a traction force is exerted on the distal link 2, thereby causing it to pivot about its pivot axis until its internal end face 6 comes to bear against the internal end face 6' of the adjacent intermediate link, which is then caused to pivot, . . . , and so on until the entire set of links has folded completely to constitute a turn that is not yet closed.

FIG. 6 shows a portion of this turn, with the distal link 4 being close to and immediately beside the proximal link 2. In this disposition, the stud 18 on the distal link 4 is facing the transverse recess 14. It then suffices for the practitioner to use an appropriate instrument to move these two links towards each other so as to cause the stud 18 to penetrate into the recess 14. The practitioner is assisted in this action by the chamfered shape 22 of the two branches 20a and 20b of the stud 18. During this penetration, and because of the chamfered shape 22, the flexible branch 20a goes beyond the abutment 15 until the abutment penetrates into the groove 23. This achieves complete and irreversible locking together of the proximal and distal links 2 and 4, and thus of the gastric ring 1 around the stomach. The practitioner can then withdraw the ancillary 26 and can confirm that the gastric ring 1 is in a closed configuration by making a tight knot between the two free ends 25 and 25' of the tie 24 at the tube fitting 16. Optionally, the knot may be tied after the threaded tube fitting 16 has been covered with a closure cap 27 that is itself pierced by a hole 28 for passing the two free ends 25 and 25' of the tie 24.

In order to make it easier to move the proximal and distal links 2 and 4 towards each other for locking purposes, with the practitioner then using equipment of the forceps type, the distal link 4 includes lateral grooving 29 in the face of the distal link 4 that is level with the stud 18 and remote from the notch 19. By positioning the ends of the two branches of the forceps one in the grooving 29 in the distal link 4 and the other in the opening 14 in the proximal link 2, the practitioner can ensure that the two branches 20a and 20b of the stud 18 are accurately positioned facing the recess 14 when the distal and proximal links 4 and 2 are face to face. It then suffices to move the two branches of the forceps towards each other to cause the stud 18 to penetrate into the recess 14 in order to achieve locking as described above.

The present invention is not limited to the specific embodiment described above. The number, configuration, and dimensions of the links are a function of the diameter of the constriction applied to the stomach. In the version described, this diameter is not adjustable, so a plurality of gastric ring models are made available to the practitioner so as to enable the most appropriate model to be selected for the particular case that is to be treated.

Although not stated explicitly in the description above, it should be observed that it is important to ensure that any ring configuration avoids presenting a sharp edge in order to avoid injuring the gastric wall. In addition, the width of the contact area between the gastric ring and the stomach must be sufficient to avoid concentrating the pressure that is exerted on the stomach. This width is preferably at least 1.5 cm to 2 cm.

In order to facilitate applying traction to the tie that enables the elongate element of the gastric ring to be folded into the form of a loop, it is preferable to use an ancillary 26 that is specially adapted. By way of example, the ancillary 26 is in the form of a tube 27 provided with a handle 28 that is fitted with a mechanical system 29, in particular a rotary or ratchet wheel 30, which engages the free ends of the tie that pass inside the tube 27 and that enables said free ends to be put under tension. It then suffices to act on said handle 28 until said tension enables the elongate element to be looped so as to bring the distal and proximal end portions close together prior to fastening them to each other.

What is claimed is:

1. A gastric ring comprising an elongate element that is deformable into a loop between a distal end portion and a proximal end portion such that the inside of the loop avoids a sharp edge which would injure the gastric wall, and closure means suitable for folding said elongate element into a loop and for securing the distal and proximal end portions to each other once they have been brought close together by deforming the elongate element into a loop, wherein at least the elongate element is made of a resorbable material.

2. A gastric ring according to claim 1, wherein at least the elongate element is made of a material that is resorbable slowly over a period of about or less than 2 years.

3. A ring according to claim 1, wherein at least the elongate element is made of a poly-hydroxy acid.

4. A ring according to claim 1, wherein the elongate element is made up of multiple juxtaposed links connected through hinged pivot axes, including a proximal link, a distal link, and intermediate links.

5. A ring according to claim 4, wherein each link has an inner face adapted for coming into contact with the stomach when the ring is put into place, and two internal end faces in which at least those portions that are situated close to the inner face are oblique and radially convergent so that during closure of the ring all of said radial portions of the internal end faces are pressed against one another and the inner faces of the links constitute a substantially continuous constriction surface.

6. A ring according to claim 5, wherein each intermediate link includes, projecting from a first internal end face, a shoulder forming a pivot axis between said link and a first adjacent link, and in its second internal end face, a recess forming a housing for the shoulder of a second adjacent link, the shoulder and the recess being of dimensions to be suitable for being mutually interengaged.

7. A ring according to claim 1, wherein the closure means comprise at least one tie secured to at least one of the proximal and distal end portions.

8. A ring according to claim 7, wherein the tie is resorbable with a resorption period that is longer than the resorption period of the elongate element.

9. A ring according to claim 4, wherein each link has two through holes, together forming in the set of links two alignments of holes for two passes of a single tie from the proximal link to the distal link along the first alignment and then from the distal link to the proximal link along the second alignment.

10. A ring according to claim 1, wherein the closure means comprise locking means formed at least in part in the proximal and distal end portions of the elongate element for locking the proximal and distal end portions together.

11. A ring according to claim 7, wherein the proximal end portion, includes a tube fitting for passing the tie or the two free ends of the tie therethrough, the tube fitting being shaped for securing to an ancillary for introducing the ring.

12. A gastric ring according to claim 1, wherein at least the elongate element is made of a material that is resorbable slowly over a period lying in the range of 16 months to 24 months.

13. A ring according to claim 1, wherein at least the elongate element is made of a lactic polyacid.

14. A ring according to claim 1, wherein at least the elongate element is made of a poly (L-lactide-co-D,L-lactide).

15. A ring according to claim 10, wherein the elongate element is made up of multiple juxtaposed links connected through hinged pivot axes, including a proximal link, a distal link, and intermediate links, and the locking means are formed in the proximal and distal links.

16. A ring according to claim 15, wherein the locking means comprise a male engagement element in one of the proximal or distal links and a female engagement element in the other proximal or distal link.

17. A ring according to claim 16, wherein the male element is a stud and the female element is a recess.

18. A ring according to claim 11, wherein the elongate element is made up of multiple juxtaposed links connected through hinged pivot axes, including a proximal link, a distal link, and intermediate links, and the tube fitting included in the proximal end portion is included in the proximal link.

19. A ring according to claim 11, wherein tube fitting is shaped for securing to an ancillary for introducing the ring by threading adapted for screw-fastening to said ancillary.

20. A ring according to claim 11, wherein the ring is connected to an ancillary constituted by a tube provided with a handle which is fitted with a mechanical system enabling the tie or the two free ends of the tie to be put under tension.

21. A ring according to claim 20, wherein the mechanical system for the ancillary is a winding or ratchet wheel.

* * * * *